United States Patent [19]

Wong et al.

[11] Patent Number: 4,741,346
[45] Date of Patent: May 3, 1988

[54] SPECIMAN COLLECTOR

[75] Inventors: Johnson N. S. Wong, Rolling Hills; Gary Watanabe, Redondo Beach, both of Calif.

[73] Assignee: Evergreen Industries, Inc., Los Angeles, Calif.

[21] Appl. No.: 874,766

[22] Filed: Jun. 16, 1986

[51] Int. Cl.$^4$ .............................................. A61B 5/00
[52] U.S. Cl. ..................................... 128/760; 435/296
[58] Field of Search ................. 128/760, 763; 4/144.1, 4/144.2, 144.4, 301, 476; 206/446, 459; 215/12 R, 303, 334; 73/864.51, 864.53, 864.91; 220/306, 307, 375; 435/296, 800; 422/99, 102

[56] References Cited

U.S. PATENT DOCUMENTS

| | | | |
|---|---|---|---|
| 3,518,164 | 6/1970 | Andelin et al. | 128/760 |
| 4,283,498 | 8/1981 | Schlesinger | 435/296 |
| 4,589,548 | 5/1986 | Fay | 435/296 |

Primary Examiner—Edward M. Coven
Assistant Examiner—Randy Citrin
Attorney, Agent, or Firm—Nilsson, Robbins, Dalgarn, Berliner, Carson & Wurst

[57] ABSTRACT

An apparatus for collecting biological fluids including a specimen vial, in which a funnel is inserted, held in a substantially upright position in a base which has a detachable wall that houses and holds a vial cap and which lid is grippable to be used to secure and/or unsecure the cap to and/or from the vial.

18 Claims, 4 Drawing Sheets

SPECIMAN COLLECTOR

BACKGROUND OF THE INVENTION

The present invention is directed to medical and laboratory equipment, more specifically, to an apparatus for collecting biological fluids.

It is typically necessary in diagnosing many diseases to collect biological fluids from a patient, e.g., sputum, blood or urine, for analysis. This is particularly true in the diagnosis of upper respiratory tract diseases. Generally, apparatus used in the collection of biological fluids, specifically sputum, include a vial held upright in a base with a funnel inserted in the vial open end.

It is important during the collection and handling of biological specimens that both the potential of specimen contamination and the spread of any infection from the specimen be minimized. Many present collection apparatus are provided in sterile packages. While this minimizes the possibility of contamination prior to use, there still remains the potential of specimen contamination during the actual collecting process. Furthermore, the sterile packaging does not reduce the potential of infection to the medical personnel who handle and come into contact with the specimen vial.

Examples of presently available specimen collecting apparatus are disclosed in U.S. Pat. Nos. 3,518,164, issued to Andelin et al and 4,283,498, issued to Schlesinger.

The apparatus disclosed in the Andelin et al. patent reference includes a specimen receptacle or vial, in which a funnel is inserted, coaxially disposed in an outer protective body which is made of a rigid material. A receptacle or vial cap is held in place within the protective body by four ribs integrally formed in the inner surface of this protective body. This cap is physically handled when being removed for mounting upon the vial. Thus, while the vial and cap may be protected from contamination during the actual specimen collection, there exists the potential for contaminating the specimen and the possible spread of infection during the procedure of sealing the vial with the cap.

The apparatus disclosed in the Schlesinger et al. patent reference includes a vial, in which a funnel is inserted, supported upright in a base. A flexible outer protective covering is provided surrounding both the vial and the base, in comparison to the rigid body disclosed in the Andelin et al. patent reference. Again, the vial cover is physically handled during the sealing operation which creates the potential of specimen contamination or the spread of infection.

Figure 6:
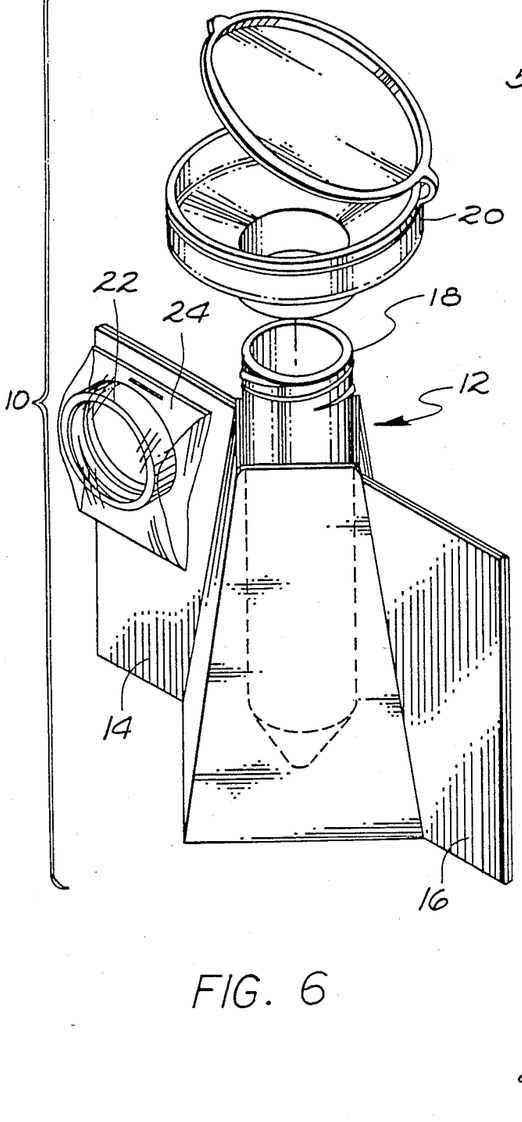
FIGS. 6 and 7 are perspective views of presently available specimen collection apparatus.
Figure 7:
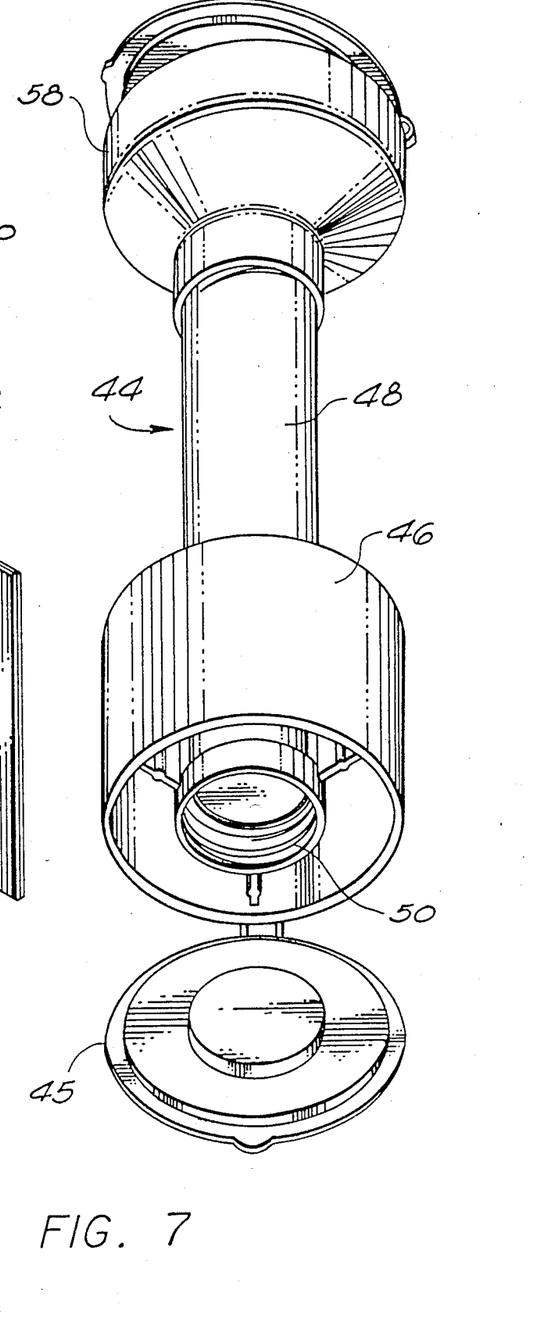

Further examples of presently available collecting apparatus are illustrated in FIGS. 6 and 7 herein.

In FIG. 6, the apparatus, as seen generally at 10, includes a hollow, frustum-shaped base 12, having a pair of support ears 14 and 16 extending laterally outward therefrom, in which a vial 18 is inserted. A funnel 20 is fitted into the opening of the vial 18, with a cap 22 attached directly to the base 12, typically by being stapled in a cellophane bag 24 to one of the support ears 14 or 16. Again, the cap 22 must be physically handled as it is removed from the cellophane bag 24 and secured to the open end of the vial 18.

In FIG. 7, another presently known collecting apparatus is seen at 44. This apparatus 44 includes a base 46, in which the specimen tube 48 is held in an upright position with a funnel 58 inserted in the tube 48 open end. The base 46 is substantially hollow and opened at its lower end. A detachable cover 45 is mounted at the base open end. A tube cap 50 is mounted inside the base 46 between three inwardly projecting ribs. After the specimen has been collected in the tube 48 the funnel 58 is removed. The appropriate medical personnel then detach the cover 45 from the base 46, remove the tube 48 from the base 46 and threadably tighten the tube 48 to the cap 50, which remains mounted in the base 46. Thus the medical personnel must physically handle the tube 48 during the sealing operation.

It can thus be seen that there remains a need to provide an apparatus for the collecting of bodily fluids, e.g., sputum, from a patient which is both convenient and which minimizes the potential contamination of the collected fluid and the spread of infection to medical personnel.

SUMMARY OF THE PRESENT INVENTION

The present invention accomplishes the foregoing objectives by providing an apparatus for collecting bodily fluids, particularly sputum. The collection apparatus of the invention generally includes a base stand which supports a specimen vial in an upright position. A funnel is inserted into the open end of the specimen vial. The base portion is a substantially hollow tubular structure to which a graspable lid is detachably secured. A vial cap is housed by this lid and positioned internally the base portion when the lid is attached thereto. This lid is dimensioned to be grasped by and allow the user to secure the cap to the specimen vial without actually touching the cap.

Specifically, an apparatus is provided for specimen collection including a substantially hollow tubular base stand. The upper end of the base stand is partially closed and formed to provide a receptacle in which a conical specimen vial can be placed and held in an upright position. A funnel is partially inserted in the open upper end of the vial. The fit of the funnel in the vial is firmer than the fit of the vial in the base. This allows the vial to be removed from the base by pulling up on the funnel. Preferably, the funnel is formed with a neck portion which surrounds and encloses the upper portion of the vial. The base stand lower end is substantially open and to which the lid housing the vial cap is detachably coupled. Preferably, the base stand has at least a first upwardly extending substantially tubular wall which at least partially surrounds the vial positioned the receptacle. The tubular wall, in combination with the preferred funnel neck portion, fully encloses the vial and minimizes the possibility of any specimen becoming lodged on the vial outer surface. This reduces the risk of spreading any infection to anyone who subsequently handles the vial. Preferably, this upwardly extending tubular wall is compressable allowing the appropriate personnel to grip the vial during the removal of the funnel and the attachment and/or removal of the cap, without actually touching the outer via surface.

In accordance with a still more preferred embodiment, the upwardly extending tubular wall is formed to allow for the visual observation of a graduation scale longitudinally provided on the vial and the amount of the specimen being collected.

BRIEF DESCRIPTION OF THE DRAWINGS

The present invention may be better understood and its numerous advantages will be apparent to those skilled in the art by reference to the accompanying drawings wherein like reference numerals refer to like elements in the several figures in which.

DESCRIPTION OF THE PREFERRED EMBODIMENTS

The present invention is directed to a specimen collecting apparatus having a base stand in which a specimen vial is held in a substantially upright position. A funnel is fitted partly into the vial open end. The base stand, in conjunction with a portion of the funnel, substantially encloses the vial, isolating the vial from the specimen being collected. A vial cap is housed on a lid which is detachable to and upon which the base stand rests. This lid is formed to be grasped by the user and also to hold the cap while coupling the cap to and/or releasing the cap from the vial, without the user having to touch the cap. This minimizes the potential of spreading infection to the medical personnel who handle the apparatus and of contaminating the specimen by the handling of the cap.

Figure 1:
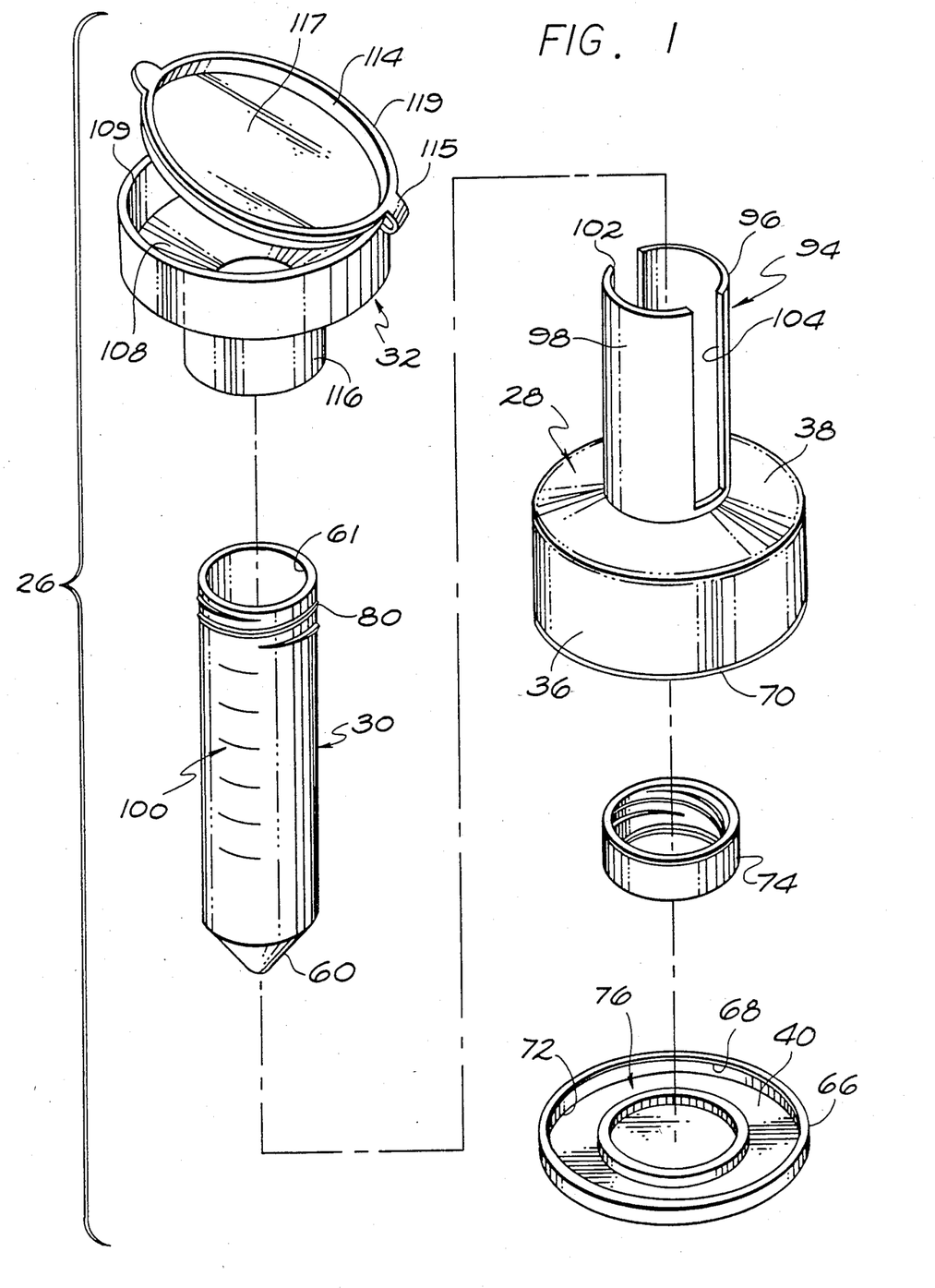
FIG. 1 is an exploded perspective view of a specimen collector in accordance with an embodiment of the invention.
Figure 2:
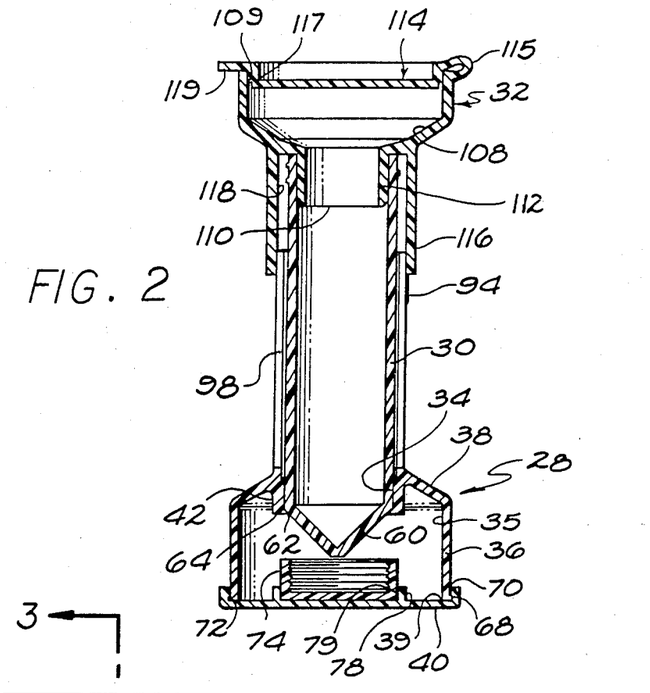
FIG. 2 is a cross-sectional view of the collector illustrated in FIG. 1.

Referring now to FIGS. 1 and 2, the apparatus of the invention is seen generally at 26. The apparatus 26 includes a base stand 28, specimen vial 30 and funnel 32. The vial 30 is a substantially elongated hollow tube having a closed lower end 60 and an opposite open end 61. A portion of the funnel 32 can be inserted in the vial open end 61. The upper surface of the vial 30, contiguous to the open end 61, is formed with threads which are threadably mateable with a threaded vial cap 74. Preferably, a graduation scale (usually a 50 millimeter graduation scale) is provided along the length of the vial 30, as indicated generally at 100.

The base stand 28 is a substantially hollow tubular structure having a circular peripheral wall 36 and an upper wall 38. This upper wall 38 is provided with a receptacle 34 in which the vial 30 can be held in a substantially upright position. A lid 40 is detachably coupled to the lower end 39 of the base stand 28 which is opened. This lid 40 is a substantially circular wall detachably coupled to the base stand 28 in any suitable manner.

In accordance with a preferred embodiment, this lid 40 has a circular lip 66 which extends generally upward about the lid 40 periphery. When the base stand 28 is placed on the lid 40 this lip 66 encicles the base stand lower end 39. The lip 66 is formed with an inwardly extending annular rib 68 that is spaced away from the surface of the lid 40 to define an annular groove 72. A mating rib 70, which is formed to extend out from the peripheral wall 36 about the lower end 39 can be placed in this groove 72. A user of the apparatus 26 places the base stand 28 onto the lid 40 so that the ribs 68 and 70 become interlocked. Typically, either the base stand 28 or the lid 40 is comprised of a resilient material to allow the ribs 68 and 70 to deflect away from each other as the base stand 28 is placed onto the lid 40. This is but one mechanism allowing the base stand 28 and lid 40 to be repeatably coupled and decoupled.

The lid 40 further includes a housing in which the vial cap 74 can be held, as indicated generally at 76. This housing 76 holds the cap 74 as it is coupled to and/or released from the vial 30 as the lid 40 is grasped by the patient or other personnel. The housing 76 is formed from a substantially ring-shaped enclosure 78 which extends generally upward from and is integral with the lid 40. The cap 74 is placed into this enclosure 78. In accordance with a preferred embodiment, the enclosure 78 is dimensioned to snugly fit the cap 74 and has an inner surface 79 which is formed to grip the outer peripheral surface of the cap 74, as the cap 74 is secured to and/or removed from the vial 30. Typically, these surfaces have cooperatively mating transverse ribs and grooves which interlock to allow the enclosure 78 to frictionally grip the cap 74 as the cap is threaded to or removed from the vial 30.

When the lid 40 is coupled to the base stand 28, the cap 74 and the housing 76 are placed in the base stand 28. This ensures that the cap 74 is isolated and free from contamination during the collecting of the specimen.

As better seen in FIG. 2, the base stand 28 upper wall 38 defines the receptacle 34 in which the lower closed end 60 of the vial 30 is placed. This receptacle 34 is defined by a peripheral wall 42 which has a lower end from which a shoulder 64 extends radially inward for a specified distance, thus forming an aperture 62. The lower end 60 of the specimen vial 30 can be placed in this receptacle 34 and partially pass through this aperture 62. The remaining portion of the vial 30 lower end 60 rests upon the shoulder 64. The receptacle 34 is dimensioned to snugly retain the vial 30 in a substantially vertical or upright position. In accordance with another embodiment, not illustrated, the vial 30 is formed with a polygonal configured skirt extending down about the lower end 60. This allows the vial 30 to be free standing. This type of formed vial 30 would be receivable in the described receptacle 34.

Preferably, the base stand 28 further includes a substantially tubular enclosure 94 which extends upward from the wall 38 about the receptacle 34. This enclosure 94 partially surrounds and encloses a portion of the vial 30, as better seen in FIG. 3. This enclosure 94 is preferably formed by two opposing upwardly extending arcuately shaped walls 96 and 98. These walls 96 and 98 are spatially separated from each other along their lengths to define first and second lognitudinally cutaways 102 and 104. These cutaways 102 and 104 run substantially the entire length of the enclosure 94. In accordance with this embodiment, these walls 96 and 98 are elastically deflectable towards and back away from each other to allow the user of the apparatus 10 to grasp a specimen vial 30 which is positioned in the enclosure 94. Furthermore, the 50 ml graduation scale 100, and the contents of the collection tube 30, can be observed through either of these cutaways 102 and 104. It should be noted that the enclosure 94 may be formed from one substantially tubular upwardly extending wall or, as preferred, one or more arcuately shaped upwardly extending walls which are spatially oriented to form one or more longitudinal elongated cutaways between them. Furthermore, the enclosure 94 may be comprised of a transparent material.

A specimen, e.g. sputum, is delivered into the specimen vial 30 via the funnel 32. The funnel 32 is formed with a tapered passageway 108 which longitudinally traverses the funnel 32 from a first larger funnel opening 109 to a second smaller funnel opening 110. The lower portion of the funnel 32 includes a neck portion 112. This neck portion 112 is dimensioned to be snugly fit in the open end 61 of the vial 30. The second smaller funnel opening 110 is provided at the lower end of the neck portion 112. A detachable cover 114 is provided to seal the open end 109 of the funnel 32. This cover 114 can be lifted off the funnel 32 when it is desired to introduce a specimen through the passageway 108 into the vial 30. Preferably this cover 114 is attached to the funnel 32 by a hinge 115. The cover 114 is formed as a cup-shaped body 117, which is dimensioned to be snugly fit in the passageway 108 contiguous to the open end 109. This cup-like body 117 has an outwardly extending flange 119 which is nested down upon the funnel 32 when the body 117 is positioned in the passageway 108.

The funnel 32 also includes a substantially tubular sleeve 116 which extends downwards, substantially coaxial with the passageway 108, about the neck portion 112. This defines an annular area 118 between the tubular sleeve 116 and neck portion 112 in which the upper portion of the vial 30 can be placed. Preferably, this sleeve 116 extends sufficiently downward to enclose at least the upper part of the tubular enclosure 94. In this manner, the specimen vial 30 is substantially enclosed by the combination of the enclosure 94 and the tubular sleeve 116. This provides a protective barrier about the vial 30 to minimize the accumulation on the exterior vial surface 30 of any specimen. This reduces the potential of transmitting infection to those who handle the vial 30.

Figure 3:
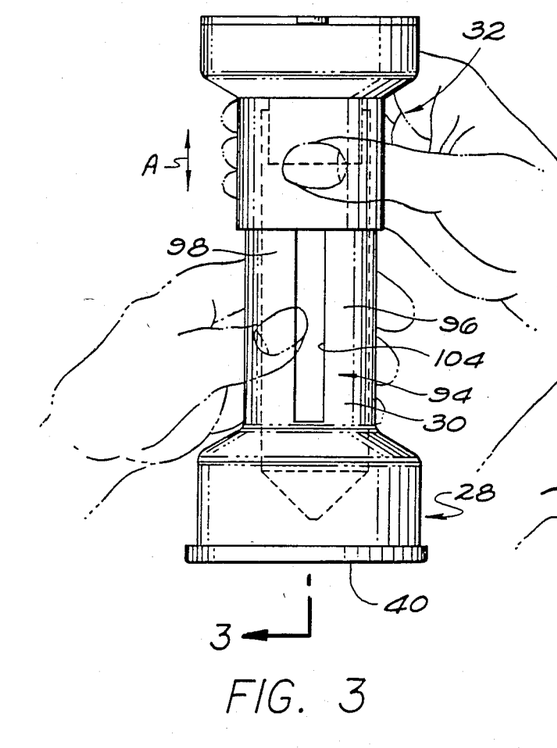
FIG. 3 is a side elevational view of a specimen collector fully assembled illustrating a stage of use of the apparatus in accordance with an embodiment of the invention.
Figure 4:
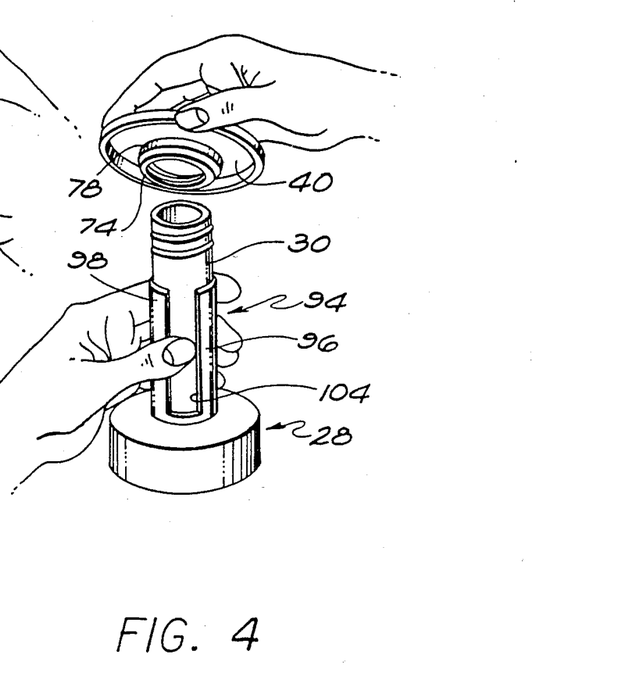
FIGS. 4 and 5 are perspective views of the specimen collector as shown in FIG. 3 at various stages during the use of the specimen collector in accordance with an embodiment of the invention.
Figure 5:
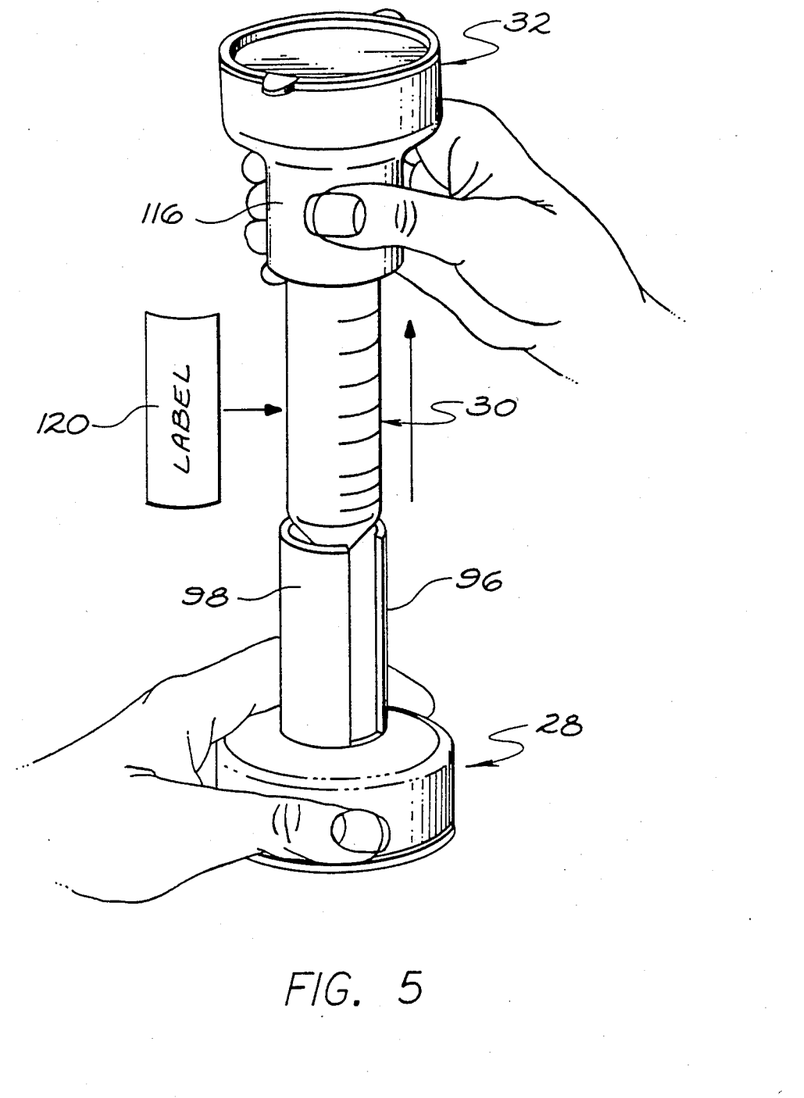

Referring now to FIGS. 3, 4 and 5 simultaneously, the procedure for collecting specimen and for sealing the vial 30 in accordance with an embodiment of the invention will now be described in detail. Typically, the fully assembled apparatus 26, with the funnel 32 inserted in the vial 30, is provided in a sealed container, not shown. This sealed container minimizes contamination of the apparatus 26 in transit, and is typically a polyethylene bag or enclosure.

The patient or appropriate medical personnel dislodges the vial 30, with the funnel 32 in place, from the base stand 28. This is accomplished, as illustrated in FIG. 5, by grasping the funnel 32 about the tubular sleeve 116 with one hand, holding the base stand 28 down with the other handle and lifting the combined vial 30 and funnel 32 assembly out of the base stand 28. The removal of the vial 309 and funnel 32 in the manner described is facilitated by providing that the fit of the funnel 32 in the vial 30 is tighter than the fit of the vial 30 in the base stand receptacle 34. That is, when the user pulls up on the funnel 32, while holding down the base 28, the vial 30 will more easily be dislodged from the base stand 28 than the funnel 32.

Once the vial 30 with the funnel 32 have been removed from the base stand 28 an appropriate marking is provided on the vial 30 outer surface to indicate the identity of the patient. Typically, a self-adhering label 120, isprovided with the assembled apparatus 26 in the polyethylene bag or enclosure. The identity of the patient and other appropriate information, e.g., the type of testing which is desired to be performed on the specimen, is written on the label. Once the label is adhered to the vial 30 surface, the vial 30 and funnel 32 assembly is reinserted in the base stand receptacle 34. Usually an appropriate medical personnel will carry out this step of the specimen-collecting operation.

The patient or appropriate medical personnel then lifts the cover 114 off from the funnel 32. A specified amount of specimen is delivered into the specimen vial 30 through the passageway 108 of the funnel 32. After the specified amount of specimen has been delivered into the specimen vial 30, as observed through either of the cutaways 102 or 104, the patient or appropriate medical personnel, removes and disposes of the funnel 32. As shown in FIG. 3, the user will grasp the vial 30, by compressing the two walls 96 and 98 inward, to retain the vial 30 in the base stand receptacle 34. As illustrated, the funnel 32 is grasped about the tubular sleeve 116 to minimize any potential contact with any specimen which may be found on the funnel 32 and/or to minimize any contamination. The funnel 32 is removed by twisting the funnel 32 off while grasping the vial 30, again by compressing the walls 96 and 98 inwards. The lid 40 is then removed from the base stand 28 and used as a capping device for threadably secure the cap 74 to the specimen vial 30. The lid 40 is then pulled off the cap 74 and mounted back upon the base stand 28, in the manner described above. Again, the patient or medical personnel will grip the vial 30 as the cap 74 is threaded to the vial 30 by compressing the walls 96 and 98 towards each other.

While the preferred embodiments have been described and illustrated, various modifications and substitutions may be made thereto without departing from the scope of the invention. Accordingly, it is to be understood that the present invention has been described by way of illustration and not limitation.

What is claimed is:

1. A specimen collecting apparatus comprising:
    a substantially elongated tubular container having a first closed end and a second open end;
    collection means which is removably secured to said container second open end for directing said specimen into said container;
    cap means formed to releasably close said container open end after removal of said collection means;
    means for supporting said container with or without said collection means in a substantially upright position; and
    graspable means releasably coupled to said supporting means, releasably holding said cap means in said supporting means when said graspable means is secured thereto, said graspable means being adapted to be grasped while holding said cap means as said closing means is coupled to and/or released from said container, whereby said graspable means aids in the coupling and/or releasing of said cap means.

2. The apparatus of claim 1 wherein said supporting means is a body defining a receptacle in which said container is received and supported in said upright position, said body further defining a hollow in which said cap means is at least partially positioned when said graspable means is coupled to said body, and wherein said collection means is sufficiently secured to said container second open end to allow said container to be removed from said body receptacle by use of said collection means.

3. The apparatus of claim 2 wherein said graspable means is a substantially planar wall releasably coupled to said body, said wall including an enclosure for housing and holding said cap means as said cap means is coupled to and/or released from said container, said wall enclosure and said cap means positioned in said body hollow when said wall is coupled to said body.

4. The apparatus of claim 3 wherein said supporting means further comprises a gripping means which extends upwards from said base means about said receptacle for substantially enclosing said container.

5. The apparatus of claim 4 wherein said gripping means comprises at least two substantially elongated walls extending upward from said body, said two walls being deflectable towards and back away from each other to allow said container to be gripped.

6. The apparatus of claim 1 wherein said supporting means comprises a substantially hollow tubular base portion defined by a substantially circular peripheral wall having an upper end connected to a wall in which a receptacle for receiving and retaining said container in said substantially upright position is formed and a lower open end.

7. The apparatus of claim 6 wherein said graspable means is a substantially planar wall which is detachably coupled to said base portion at said peripheral wall open end, said planar wall including a means for housing and holding said cap means as said closing means is coupled and/or released from said container, said housing means further positioning said cap means in said base portion when said planar wall is coupled to said base portion.

8. The apparatus of claim 7 wherein said housing and holding means comprises a substantially circular enclosure integrally formed in said planar wall in which said cap means can be placed, said circular enclosure including means for engaging said cap means positioned in said circular enclosure as said cap means is coupled and/or released from said container.

9. The apparatus of claim 8 wherein said cap means is a substantially circular threaded cap.

10. The apparatus of claim 9 wherein at least a portion of said planar wall is substantially larger in width than said circular enclosure, whereby said larger wall portion is grasped as said cap means is coupled and/or released from said container.

11. The apparatus of claim 9 wherein said planar wall is substantially circular and has a diameter larger than said circular enclosure diameter.

12. The apparatus of claim 11 wherein said engaging means comprises an inner peripheral surface on said planar wall enclosure releasably engaging an outer peripheral surface of said cap means as said cap means is coupled to and/or released from said container.

13. The apparatus of claim 12 wherein said base portion further includes two substantially arcuately shaped walls which extend upwards about said base portion upper wall receptacle to at least partially enclose said container positioned in said upper wall receptacle, said walls being deflectable towards and back away from each other to allow said container to be gripped, whereby said container is held in said base portion when said collection means is removed therefrom and/or when said cap means is coupled and/or removed from said container.

14. The apparatus of claim 13 wherein said collection means is a funnel having open upper and bottom ends with a passageway therebetween, said funnel having a substantially tubular neck portion extending down from said bottom end which is snugly receivable in said container open end sufficiently to allow said container to be removed from said supporting means by use of said funnel.

15. The apparatus of claim 14 wherein said funnel further includes a substantially tubular collar extending downward and substantially coaxial with said neck portion, said collar spatially separated from said neck portion to allow at least a portion of said container to be placed therebetween.

16. The apparatus of claim 15 wherein at least a portion of said upwardly extending walls is positioned between said tubular collar and said funnel neck portion with said container.

17. The apparatus of claim 16 wherein said funnel further includes a cover releasably coupled to said funnel and fitted into said funnel upper open end.

18. The apparatus of claim 13 wherein said container further includes a scale formed along a longitudinal length of said container, and wherein said arcuately shaped walls are formed with two opposing vertical edges, with said vertical edges of adjacently positioned walls being arranged in a spaced apart relationship to allow for the visualization of said graduation scale when said graduation scale is positioned between said spaced apart wall edges.

* * * * *

UNITED STATES PATENT AND TRADEMARK OFFICE
CERTIFICATE OF CORRECTION

PATENT NO. : 4,741,346

DATED : May 3, 1988

INVENTOR(S) : Wong and Watanabe

It is certified that error appears in the above-identified patent and that said Letters Patent is hereby corrected as shown below:

Column 2, line 58, delete "via" and insert --vial--.

Column 7, line 26, delete "closing" and insert --cap--.

Column 8, line 39, before "scale" and insert --graduated--.

Signed and Sealed this

Twentieth Day of September, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,741,346
DATED      : MAY 3, 1988
INVENTOR(S) : JOHNSON N.S. WONG AND GARY WATANABE

It is certified that error appears in the above-indentified patent and that said Letters Patent is hereby corrected as shown below:

Delete "closing means" in Claim 1, column 6, line 52 and substitute therefore --cap means--.

Title page item [54], and column 1, line 2, should read --SPECIMEN--.

Signed and Sealed this

Tenth Day of December, 1996

Attest:

BRUCE LEHMAN

*Attesting Officer*      *Commissioner of Patents and Trademarks*